US00PP31149P2

(12) United States Plant Patent
Sterling et al.

(10) Patent No.: US PP31,149 P2
(45) Date of Patent: Dec. 3, 2019

(54) ***METASEQUOIA* TREE NAMED 'URBAN SPIRE'**

(50) Latin Name: *Metasequoia glyptostroboides*
Varietal Denomination: Urban Spire

(71) Applicants: Timothy Sterling, Malvern, PA (US); Andrew Schenck, Malvern, PA (US)

(72) Inventors: Timothy Sterling, Malvern, PA (US); Andrew Schenck, Malvern, PA (US)

( * ) Notice: Subject to any disclaimer, the term of this patent is extended or adjusted under 35 U.S.C. 154(b) by 0 days.

(21) Appl. No.: 15/998,204

(22) Filed: Jul. 12, 2018

(51) Int. Cl.
*A01H 5/00* (2018.01)
*A01H 7/00* (2006.01)

(52) U.S. Cl.
USPC ..... Plt./213

(58) Field of Classification Search
USPC ..... Plt./213
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Metasequoia* cultivar named 'Urban Spire' is disclosed, characterized by a distinctive upright, narrow tree form. Branches are held at angles of approximately 45 degrees or less, forming the distinctive narrow shape. The tree is well suited for small properties, street applications or as a specimen in the landscape. The new cultivar is a *Metasequoia*, suitable for various landscape purposes.

2 Drawing Sheets

Latin name of the genus and species: *Metasequoia glyptostroboides*.

Variety denomination: 'Urban Spire'.

BACKGROUND OF THE INVENTION

The new cultivar is a product of chance discovery by the inventors, Timothy Sterling and Andrew Schenk. This new variety, hereinafter referred to as 'Urban Spire', was selected as single seedling among a commercial planting of numerous seedling trees of unpatented, unnamed *Metasequoia glyptostroboides*. The novel variety was discovered in a commercial nursery in Malvern, Pa. during August of 2007.

After identifying the new variety as a potentially interesting selection, first propagation of 'Urban Spire' occurred by bud wood graft during September of 2012 at a commercial nursery in Malvern, Pa. The inventor continued controlled testing and propagation, assessing stability of the unique characteristics of this variety. Three generations have been reproduced and have shown that the unique features of this cultivar are stable and reproduced true to type.

SUMMARY OF THE INVENTION

The cultivar 'Urban Spire' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Urban Spire' These characteristics in combination distinguish 'Urban Spire' as a new and distinct *Metasequoia* cultivar:

1. Slender, upright growth habit.
2. Suitability as a street tree or specimen.
3. Suitability for smaller landscape situations.

COMPARISON TO PARENT VARIETY

'Urban Spire' is similar in most horticultural characteristics to the parent variety. Trees of the new cultivar 'Urban Spire' however, are distinctively more narrow with more acute branching angles.

COMMERCIAL COMPARISON

In addition to the seed parent, 'Urban Spire' can be compared to the commercial variety *Metasequoia glyptostroboides* 'Sheridan Spire', unpatented. The varieties are similar in most horticultural characteristics, however, trees of 'Urban Spire' differ in the following:

1. The new variety has a denser habit with shorter growth nodes.
2. Branch angle of the new variety is 45 degrees from center, or more acute, 'Sheridan Spire' has a broader branch angle.
3. Overall habit of the new variety is narrower and more upright than 'Sheridan Spire'.

'Urban Spire' can be compared to the commercial variety *Metasequoia glyptostroboides* 'National', unpatented. The varieties are similar in most horticultural characteristics, however, trees of 'Urban Spire' differ in the following:

1. The new variety has a denser habit with shorter growth nodes.
2. Branch angle of the new variety is 45 degrees from center, or more acute, 'National' has a broader branch angle.
3. Overall habit of the new variety is narrower and more upright than 'National'.

BRIEF DESCRIPTION OF THE PHOTOGRAPHS

Figure 1:
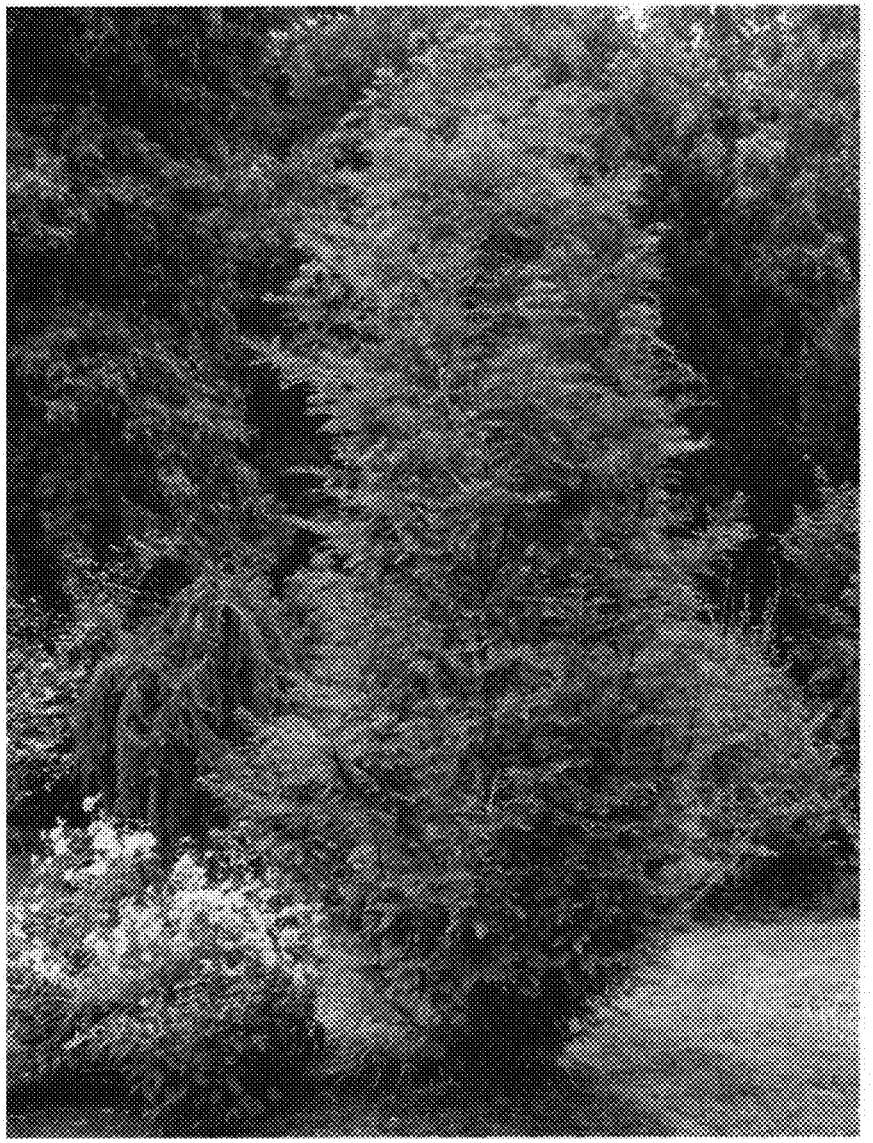

The accompanying photograph in FIG. 1 illustrates in full color a typical tree of 'Urban Spire' grown outdoors in Malvern, Pa. at approximately 10 years of age, during Summer.

Figure 2:
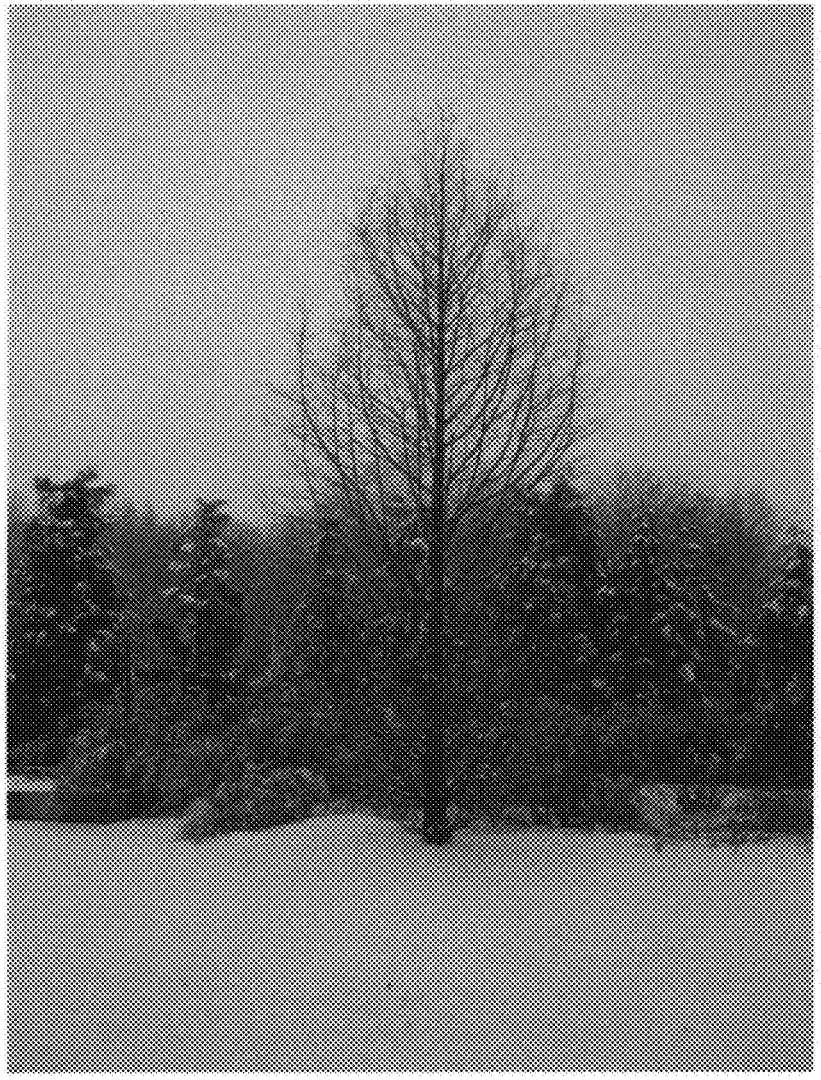

FIG. 2 illustrates the same tree during the Winter, while deciduous. FIG. 2 illustrates the acute angle of the branches, better seen without foliage. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Urban Spire' trees grown outdoors in Malvern, Pa. Trees are approximately 10 years years old, planted in the ground. Measurements and numerical values represent averages of typical tree types. Temperatures ranged from approximately −17° C. to 35° C. during the day and −17° C. to 26° C.

Botanical classification: *Metasequoia glyptostroboides* 'Urban Spire'.

PROPAGATION

Typical Propagation method: Bud wood graft.

TREE

Growth Habit: Upright, columnar deciduous tree.
Height: Approximately 25 feet after 10 years.
Tree Spread: Approximately 12 feet after 10 years.
Typical Growth Rate: Moderate.
Trunk Color: Near RHS greyed orange 173 A.
Trunk Diameter (give height measured at): 12" at 8" above ground level.
Trunk Texture: sinewy.
Branching Characteristics: 45 degree, or less angle from trunk.
Diameter of Lateral Branches: Varies, with an average range between 0.4 to 4 inches.
Texture of Lateral Branches: Shredded.
Color of Lateral Branches: Near RHS Greyed-Orange 173 A.
Strength of Lateral Branches: Strong and flexible, no snow, ice or wind damage observed.
Internode length: Average 1".
Root Description: Fibrous, very well branched. Colored near RHS Brown N199B.

FOLIAGE

Leaf:
- *Arrangement.*—opposite.
- *Average Length.*—3 to 4 inches.
- *Average Width.*—0.75 to 1 inch.
- *Shape.*—Oblong.

Individual Needles:
- *Arrangement.*—Opposite.
- *Average Length.*—¼ to ½ inch.
- *Average Width.*—1/16 up to ⅛ inch.
- *Shape of blade.*—Linear.
- *Apex.*—Acute.
- *Base.*—Obtuse.
- *Attachment.*—Sessile.
- *Margin.*—Entire.
- *Texture of top surface.*—Glabrous.
- *Texture of bottom surface.*—Glabrous.
- *Color.*—Young foliage upper side: Near RHS Green 137 C. Young foliage under side: Near RHS Green 137 C. Mature foliage upper side: Near RHS Green 135 A. Mature foliage under side: Near RHS Green 138 A. Fall foliage upper side: Near RHS Greyed-Orange N170 A. Fall foliage under side: Near RHS Greyed-Orange 168 C.
- *Venation.*—Type: Linear. Venation color: Indistinguishable from foliage color.
- *Petiole.*—Length: About ½ inch. Diameter: About 1/16 inch. Color: Near RHS Green 137C. Texture: Glabrous.

FLOWER

Flowering not observed.
Cone not observed to date.

OTHER CHARACTERISTICS

Disease and Pest Resistance: Neither resistance nor susceptibility observed.
Drought Tolerance: Tolerates drought once established.
Temperature Tolerance: Observed to tolerate temperatures between −17° C. and 40° C.

What is claimed is:

1. A new and distinct *Metasequoia* tree named 'Urban Spire' as herein illustrated and described.

* * * * *